US00PP22134P2

(12) United States Plant Patent
Stringer

(10) Patent No.: US PP22,134 P2
(45) Date of Patent: Sep. 6, 2011

(54) ***KNIPHOFIA* PLANT NAMED 'ELVIRA'**

(50) Latin Name: *Kniphofia uvaria*
Varietal Denomination: 'Elvira'

(76) Inventor: Paul Stringer, Tilehurst Reading (GB)

( * ) Notice: Subject to any disclaimer, the term of this patent is extended or adjusted under 35 U.S.C. 154(b) by 0 days.

(21) Appl. No.: 12/924,017

(22) Filed: Sep. 17, 2010

(51) Int. Cl.
*A01H 5/00* (2006.01)

(52) U.S. Cl. ..... Plt./443

(58) Field of Classification Search ..... Plt./443
See application file for complete search history.

*Primary Examiner* — Kent L Bell

(74) *Attorney, Agent, or Firm* — C. A. Whealy

(57) ABSTRACT

A new and distinct cultivar of *Kniphofia* plant named 'Elvira', characterized by its tall and upright growth habit; vigorous growth habit; long flowering period; greyed orange-colored flowers; and good garden performance.

1 Drawing Sheet

Botanical designation: *Kniphofia uvaria.*
Cultivar denomination: 'ELVIRA'.

BACKGROUND OF THE INVENTION

The present invention relates to a new and distinct cultivar of *Kniphofia* plant, botanically known as *Kniphofia uvaria* and hereinafter referred to by the name 'Elvira'.

The new *Kniphofia* plant originated from an open-pollination of an unnamed selection of *Kniphofia uvaria*, not patented, as the female, or seed parent and an unknown selection of *Kniphofia uvaria* as the male, or pollen, parent. The new *Kniphofia* plant was discovered and selected by the Inventor in 1997 as a single plant within the progeny of the stated open-pollination in a controlled environment in Berkshire, United Kingdom.

Asexual reproduction of the new *Kniphofia* plant by divisions in a controlled environment in Berkshire, United Kingdom has shown that the unique features of this new *Kniphofia* plant are stable and reproduced true to type in successive generations.

SUMMARY OF THE INVENTION

Plants of the new *Kniphofia* have not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Elvira'. These characteristics in combination distinguish 'Elvira' as a new and distinct cultivar of *Kniphofia* plant:

1. Tall and upright growth habit.
2. Vigorous growth habit.
3. Long flowering period.
4. Greyed orange-colored flowers.
5. Good garden performance.

Plants of the new *Kniphofia* can be compared to plants of the female parent selection. Plants of the new *Kniphofia* differ from plants of the female parent selection primarily in plant size and vigor.

Plants of the new *Kniphofia* can be compared to plants of *Kniphofia uvaria* 'Fiery Fred', not patented. In side-by-side comparisons conducted in Bressingham, United Kingdom, plants of the new *Kniphofia* differed from plants of 'Fiery Fred' in the following characteristics:

1. Plants of the new *Kniphofia* were shorter than plants of 'Fiery Fred'.
2. Plants of the new *Kniphofia* and 'Fiery Fred' differed in flower color as plants of 'Fiery Fred' had greenish orange-colored flowers.

BRIEF DESCRIPTION OF THE PHOTOGRAPH

The accompanying colored photograph illustrates the overall appearance of the new *Kniphofia* plant showing the colors as true as it is reasonably possible to obtain in colored reproductions of this type. Colors in the photograph may differ slightly from the color values cited in the detailed botanical description which accurately describe the colors of the new *Kniphofia* plant. The photograph comprises a side perspective view of typical flowering plants of 'Elvira' grown in an outdoor nursery.

DETAILED BOTANICAL DESCRIPTION

The aforementioned photograph and following observations, measurements and values describe plants grown during the early autumn in an outdoor nursery in Bressingham, United Kingdom and under conditions which approximate commercial production. During the production of the plants, day temperatures averaged 21° C. and night temperatures averaged 10° C. Plants were three years old when the photograph and description were taken. In the following description, color references are made to The Royal Horticultural Society Colour Chart, 1996 Edition, except where general terms of ordinary dictionary significance are used.

Botanical classification: *Kniphofia uvaria* 'Elvira'.

Parentage:

*Female, or seed, parent.*—Unnamed selection of *Kniphofia uvaria*, not patented.

*Male, or pollen, parent.*—Unknown selection of *Kniphofia uvaria*, not patented.

Propagation:

*Type.*—By divisions.

*Time to initiate roots, summer.*—About 15 days at 21° C.

*Time to initiate roots, winter.*—About 40 days at 21° C.

*Time to produce a rooted young plant, summer.*—About one month at 21° C.

*Time to produce a rooted young plant, winter.*—About three months at 5° C.

*Root description.*—Medium to thick, fleshy; color, close to 163A to 163C.

*Rooting habit.*—Freely branching; moderately dense.

Plant description:

*Plant and growth habit.*—Herbaceous perennial; tall and upright growth habit; basal rosette of leaves; flowering stems developing from the center of the basal rosette of leaves; vigorous growth habit.

*Plant height, soil level to top of foliar plane.*—About 70 cm.

*Plant height, soil level to top of inflorescences.*—About 100 cm.

*Plant diameter.*—About 30 cm to 50 cm.

Foliage description:

*Arrangement.*—Alternate; simple; sessile.

*Length.*—About 40 cm to 70 cm.

*Width.*—About 1 cm.

*Shape.*—Lanceolate; keeled.

*Apex.*—Acute.

*Base.*—Cuneate.

*Margin.*—Finely serrate; ciliate.

*Texture, upper and lower surfaces.*—Slightly pubescent.

*Venation pattern.*—Parallel.

*Color.*—Developing leaves, upper and lower surfaces: Close to 144B to 144C. Fully expanded leaves, upper surface: Close to 137C; towards the base, close to 158C; venation, close to 137C. Fully expanded leaves, lower surface: Close to 137D; towards the base, close to 158C; venation, close to 137D.

Flower description:

*Flower arrangement and habit.*—Single tubular flowers arranged on upright terminal racemes; freely flowering habit with about 70 to 100 flowers per inflorescence; flowers face outwardly to downwardly.

*Fragrance.*—None detected.

*Natural flowering season.*—Plants begin flowering about 150 days after planting; long flowering period, plants flower continuously from July to September in the United Kingdom.

*Flower longevity.*—Individual flowers last about ten days on the plant; inflorescences last about 14 to 18 days on the plant; flowers not persistent.

*Inflorescence height.*—About 10 cm to 20 cm.

*Inflorescence diameter.*—About 4 cm.

*Flower length.*—About 2 cm to 4 cm.

*Flower diameter.*—About 3 mm to 4 mm.

*Flower bud.*—Length: About 5 mm to 10 mm. Diameter: About 2 mm to 4 mm. Shape: Cylindrical. Color: Close to 174A lightly flushed with close to 137A.

*Petals.*—Arrangement: Six petals fused into a tube. Length: About 2 cm to 4 cm. Width: About 3 mm to 5 mm. Lobe shape: Roughly ovate. Apex: Obtuse. Margin: Entire. Texture, upper and lower surfaces: Smooth, glabrous. Color: When opening, outer surface: Close to 169A. When opening, inner surface: Close to 170C. Fully opened, outer surface: Close to 169B; color becoming closer to 163C with development. Fully opened, inner surface: Close to 169D; color becoming closer to 163D with development.

*Sepals.*—Quantity per flower: Numerous. Length: About 2 mm to 5 mm. Width: About 2 mm. Shape: Lanceolate. Apex: Acute. Base: Cuneate. Margin: Entire. Texture, upper and lower surfaces: Pubescent. Color, upper surface: Close to 164B. Color, lower surface: Close to 164C.

*Peduncles.*—Length: About 70 cm to 100 cm. Diameter: About 5 mm to 15 mm. Strength: Strong. Aspect: Erect. Texture: Smooth, glabrous. Color: Close to 144A; with development, color becomes closer to 144B flushed with close to 169A.

*Pedicels.*—Length: About 4 mm. Diameter: About 0.5 mm to 1 mm. Strength: Strong, wiry. Aspect: Drooping. Texture: Smooth, glabrous. Color: Close to 163B.

*Reproductive organs.*—Stamens: Quantity: Six per flower. Filament length: About 2 cm. Filament color: Close to 163C. Anther shape: Oblong. Anther length: About 2 mm. Anther color: Close to 16A. Pollen amount: Scarce. Pollen color: Close to 16B. Pistils: Quantity: One per flower. Pistil length: About 2.5 cm. Style length: About 2.5 cm. Style color: Close to 163D. Stigma shape: Lanceolate. Stigma color: Close to 163D. Ovary color: Close to 16B. Seeds: Length: About 2 mm. Diameter: About 0.5 mm. Color: Close to 174A.

Garden performance: Plants of the new *Kniphofia* have been observed to have good garden performance and tolerate wind, rain, high temperatures of 35° C. and hardy to USDA Hardiness Zone 6.

Pathogen/pest resistance: Plants of the new *Kniphofia* have not been observed to be resistant to pathogens and pests common to *Kniphofia*.

It is claimed:

1. A new and distinct *Kniphofia* plant named 'Elvira' as illustrated and described.

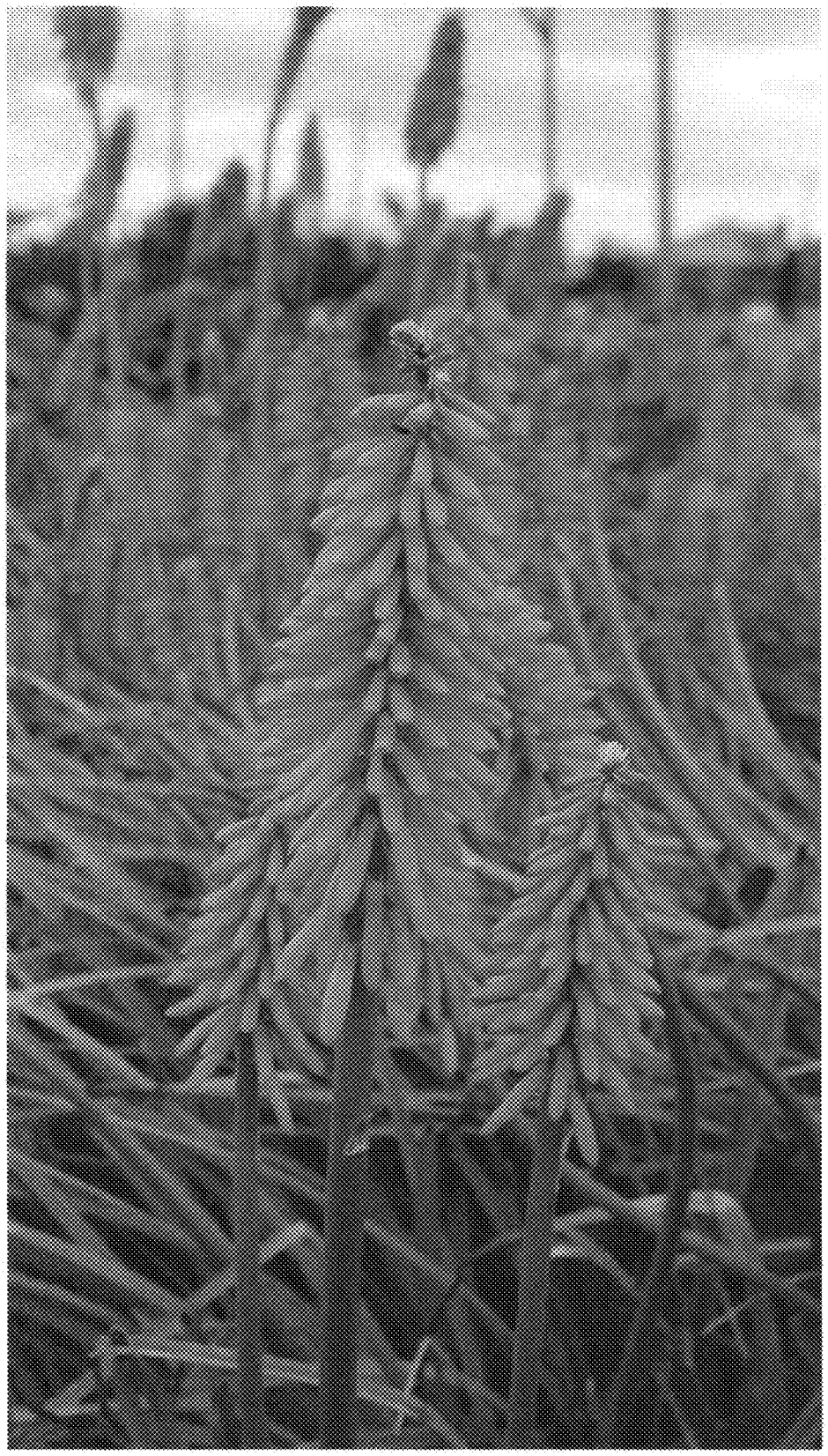

* * * * *